US012514574B2

(12) United States Patent
Yassinzadeh

(10) Patent No.: US 12,514,574 B2
(45) Date of Patent: *Jan. 6, 2026

(54) CATHETER WITH SEALED HYDRATABLE HEMOSTATIC OCCLUSION ELEMENT

(71) Applicant: Cardiva Medical, Inc., Santa Clara, CA (US)

(72) Inventor: Zia Yassinzadeh, San Jose, CA (US)

(73) Assignee: Cardiva Medical, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,485

(22) Filed: Jun. 6, 2023

(65) Prior Publication Data

US 2023/0309980 A1 Oct. 5, 2023

Related U.S. Application Data

(63) Continuation of application No. 16/997,650, filed on Aug. 19, 2020, now Pat. No. 11,690,608, which is a (Continued)

(51) Int. Cl.

*A61B 17/03* (2006.01)
*A61B 17/00* (2006.01)
*A61B 17/22* (2006.01)

(52) U.S. Cl.

CPC .................... *A61B 17/0057* (2013.01); *A61B 2017/00623* (2013.01); *A61B 2017/00654* (2013.01);

(Continued)

(58) Field of Classification Search

CPC ...... A61B 17/0057; A61B 2017/00575; A61B 2017/00597; A61B 2017/00623;

(Continued)

(56) References Cited

U.S. PATENT DOCUMENTS 4,744,364 A 5/1988 Kensey
5,061,271 A 10/1991 Van Zile (Continued)

FOREIGN PATENT DOCUMENTS

WO 2010002918 A1 1/2010
WO 2013033477 A1 3/2013

OTHER PUBLICATIONS

Office Action dated Dec. 20, 2017 for U.S. Appl. No. 13/224,539.

(Continued)

*Primary Examiner* — Todd J Scherbel

(74) *Attorney, Agent, or Firm* — Nutter McClennen & Fish LLP

(57) ABSTRACT

Apparatus for sealing a vascular wall penetration disposed at the end of the tissue tract comprises a shaft, an optional occlusion element, a hydratable hemostatic implant, and a protective sleeve. The apparatus is deployed through the tissue tract with the occlusion element optionally occluding the vascular wall penetration and inhibiting backbleeding therethrough. The hydratable hemostatic implant, which will typically be a biodegradable polymer such as collagen carrying an anti-proliferative agent or coagulation promoter, will then be deployed from the sealing apparatus by retracting the protective sleeve and left in place to enhance closure of the vascular wall penetration with minimum scarring. The hydratable implant will be protected from premature hydration and swelling by a soluble plug covering the implant's distal end prior to sleeve retraction.

20 Claims, 14 Drawing Sheets

Related U.S. Application Data continuation of application No. 15/920,372, filed on Mar. 13, 2018, now Pat. No. 10,779,808, which is a continuation of application No. 13/224,539, filed on Sep. 2, 2011, now abandoned.

(52) U.S. Cl.
CPC ............... *A61B 2017/00898* (2013.01); *A61B 2017/22067* (2013.01)

(58) Field of Classification Search
CPC ........... A61B 2017/00637; A61B 2017/00641; A61B 2017/00654; A61B 2017/00676; A61B 2017/00898
See application file for complete search history.

(56) References Cited

U.S. PATENT DOCUMENTS

| | | | | |
|---|---|---|---|---|
| 5,290,310 | A | 3/1994 | Makower et al. | |
| 5,419,765 | A | 5/1995 | Weldon et al. | |
| 5,728,133 | A | 3/1998 | Kontos | |
| 6,554,851 | B1 | 4/2003 | Palasis et al. | |
| 6,610,026 | B2 | 8/2003 | Cragg et al. | |
| 6,699,262 | B2 | 3/2004 | Redmond et al. | |
| 6,989,022 | B2 | 1/2006 | Nowakowski | |
| 7,025,776 | B1 | 4/2006 | Houser et al. | |
| 7,232,454 | B2 | 6/2007 | Rousseau | |
| 7,335,219 | B1 | 2/2008 | Ashby et al. | |
| 7,361,183 | B2 | 4/2008 | Ginn | |
| 7,691,127 | B2 | 4/2010 | Yassinzadeh | |
| 9,039,735 | B2 | 5/2015 | Khosravi et al. | |
| 10,213,191 | B2 | 2/2019 | Khosravi et al. | |
| 10,779,808 | B2 * | 9/2020 | Yassinzadeh | A61B 17/0057 |
| 11,690,608 | B2 * | 7/2023 | Yassinzadeh | A61B 17/0057 606/213 |
| 2003/0125766 | A1 | 7/2003 | Ding | |
| 2004/0267308 | A1 | 12/2004 | Bagaoisan et al. | |
| 2005/0004158 | A1 | 1/2005 | Iyer et al. | |
| 2005/0038472 | A1 | 2/2005 | Furst | |
| 2006/0088570 | A1 | 4/2006 | Cruise et al. | |
| 2007/0032804 | A1 | 2/2007 | Modesitt | |
| 2007/0060895 | A1 | 3/2007 | Sibbitt et al. | |
| 2007/0123817 | A1 | 5/2007 | Khosravi et al. | |
| 2007/0196421 | A1 | 8/2007 | Hunter et al. | |
| 2007/0299043 | A1 | 12/2007 | Hunter et al. | |
| 2008/0039362 | A1 | 2/2008 | Shebuski et al. | |
| 2009/0035351 | A1 | 2/2009 | Berglund et al. | |
| 2010/0168767 | A1 | 7/2010 | Yassinzadeh et al. | |
| 2010/0280546 | A1 | 11/2010 | Campbell et al. | |
| 2012/0209321 | A1 | 8/2012 | Yassinzadeh et al. | |
| 2013/0060279 | A1 | 3/2013 | Yassinzadeh | |
| 2018/0221006 | A1 | 8/2018 | Yassinzadeh | |
| 2021/0204924 | A1 | 7/2021 | Yassinzadeh | |

OTHER PUBLICATIONS

Final Office action dated Dec. 13, 2019 for U.S. Appl. No. 15/920,372.
International search report and opinion dated Nov. 13, 2012 for PCT/US2012/053251.
Notice of allowance dated May 20, 2020 for U.S. Appl. No. 15/920,372.
Office action dated Oct. 24, 2019 for U.S. Appl. No. 15/920,372.

* cited by examiner

CATHETER WITH SEALED HYDRATABLE HEMOSTATIC OCCLUSION ELEMENT

CROSS-REFERENCE

This application is a continuation of U.S. patent application Ser. No. 16/997,650, filed Aug. 19, 2020, which is a continuation of U.S. patent application Ser. No. 15/920,372, now U.S. Pat. No. 10,779,808, filed Mar. 13, 2018, which is a continuation of U.S. patent application Ser. No. 13/224,539, filed Sep. 2, 2011, the entire content of which is incorporated herein by reference.

BACKGROUND OF THE INVENTION

1. Field of the Invention

The present invention relates generally to medical devices and methods. More particularly, the present invention relates to apparatus and protocols for closing arteriotomies and other vascular wall penetrations.

Angiography, angioplasty, atherectomy, and a number of other vascular and cardiovascular procedures are performed intravascularly and require percutaneous access into the patient's vasculature, most often into the arterial vasculature. The most common technique for achieving percutaneous access is called the Seldinger technique, where access to an artery, typically the femoral artery in the groin, is first established using a needle to form a "tract," i.e., a passage through the tissue overlying the blood vessel. The needle tract is then dilated, and an access sheath is placed into the dilated tract and through a penetration in the vascular wall, such as an arteriotomy to allow the introduction of guidewires, interventional catheters, catheter exchange, and the like to perform the desired procedure.

Once the desired procedure is completed, the access sheath must be removed and the arteriotomy or other vascular wall penetration closed. For many years, such closure was achieved by applying manual pressure onto the patient's skin over the site of the vascular wall penetration. Patients, however, have often been heparinized to limit the risk of thrombosis during the procedure, and clotting of the vascular wall penetration can often take an extended period, particularly when the penetration is relatively large for performing procedures needing larger diameter catheters. For these reasons, improved methods for closing and sealing vascular wall penetrations have been sought.

In the last decade, a variety of new procedures and devices have been introduced to more effectively seal the arteriotomies and other vascular wall penetrations associated with percutaneous intravascular access. Some of the new protocols rely on suturing, others rely on clipping, plug placement, energy-based closure, and the like. One problem with many of the new procedures, however, is that they leave material behind, and/or induce scar formation at the access site. Both the leaving of materials and the formation of scar tissue can be problematic, particularly if the patient requires subsequent access to the same vascular site for performance of another vascular or cardiovascular procedure.

For these reasons, it would be advantageous to provide protocols and apparatus which would leave no material behind and which would further limit the likelihood of forming scar tissue after the procedure is complete. One device that can meet these objectives is described in commonly owned published U.S. Patent Application 2010/0168767, the full disclosure of which is incorporated herein by reference. The '767 application describes an apparatus and method for sealing a blood vessel wall penetration with little or no material being left permanently behind and with a reduced likelihood of scar tissue formation. The device places a hemostatic resorbable implant in the tissue tract at a location over the vascular wall penetration while the penetration is typically closed by an expansible occlusion element present in the blood vessel lumen. The hemostatic implant is hydratable so that it will swell and fully occlude the tissue tract when exposed by retraction of a protective sleeve. When used with temporary hemostasis in the blood vessel lumen, the hydratable hemostatic implant increases the likelihood that even relatively large vascular penetrations can be successfully closed and sealed without the need to leave permanent implants on the blood vessel wall or in the tissue tract.

Although highly promising, the devices described in the '767 application can suffer from premature hydration of the hemostatic implant carried by the closure device. The hemostatic implant is typically a swellable collagen or other biopolymer carried beneath the retractable protective sleeve, and blood or other fluids from the tissue tract can penetrate the region between the protective sleeve and device shaft, causing the hemostatic implant to imbibe fluids and begin to swell asymmetrically even before the protective sleeve is retracted. Such swelling can make retraction of the sleeve difficult, and deployment of an unevenly expanded implant (which occurs as the distal end nearest the open end of the protective sleeve can absorb fluid first and expand more rapidly than other portions of the implant), which can distort the implant as it deploys and compromise the resulting occlusion.

For these reasons, it would be desirable to provide improved methods and systems for deploying hydratable hemostatic implants within a tissue tract in order to achieve closure of vascular wall penetrations. It would be particularly desirable if such methods and devices were compatible with deployment of temporary occlusion elements within the blood vessel lumen, and in particular if such methods and devices reduced the risk of premature implant hydration and swelling which can occur prior to withdrawing the protective sleeve. At least some of these objectives will be met by the inventions described herein below.

2. Description of the Background Art

US2010/0168767 is described above. U.S. Pat. No. 7,335,219 describes a device for delivering a plug of hemostatic material to a location just above a blood vessel wall penetration. The hemostatic material is encapsulated in a dissolvable structure and a non-expandable control tip assembly helps advance the device through the tissue tract and may also provide hemostasis and bleedback. US2007/0123817 describes an apparatus for sealing a vascular wall penetration which releases a porous lyophilized hydrogel into the tissue tract above the puncture. Other apparatus for closing blood vessel wall punctures are described in U.S. Pat. Nos. 4,744,364; 5,061,271; 5,728,133; and 7,361,183 and U.S. Published Patent Application Nos. 2003/0125766; 2004/0267308; 2006/0088570; 2007/0196421; and 2007/0299043. The incorporation of anti-proliferative materials in hemostatic materials for blood vessel closure and other purposes is described in U.S. Pat. Nos. 7,025,776 and 7,232,454; 6,554,851; and U.S. Published Patent Application Nos. 2005/0004158; 2005/0038472; 2007/0060895/2007/0032804; and 2008/0039362.

BRIEF SUMMARY OF THE INVENTION

The present invention provides apparatus and methods for sealing a blood vessel wall penetration with little or no material being permanently left behind and with a reduced likelihood of scar tissue formation. The invention relies on placing a hydratable hemostatic implant in the tissue tract at a location over the vascular wall penetration, usually while the penetration is temporarily closed with an expansible occlusion element present in the blood vessel lumen. By “hydratable hemostatic implant” it is meant that the implant will initially be in a non-hydrated condition with an initial volume and cross sectional area (profile) selected to allow introduction through the tissue tract to a position over the vessel wall penetration. While being delivered, the hydratable hemostatic implant will be covered with a protective sleeve to prevent exposure to blood and other body fluids in the tissue tract, leaving the implant in an essentially non-hydrated condition. The hydratable hemostatic implant is preferably biodegradable, typically over a period of less than one year, preferably over a period of less than six months, more preferably less than three months, and may carry an anti-proliferative agent to reduce scar formation. Additionally or alternatively, the implant may carry a coagulation promoter to accelerate hemostasis and/or radiopaque material to enhance visualization. The use of the hemostatic implant together with the temporary hemostasis provided by the occlusion element increases the likelihood that even relatively large vascular penetrations can be successfully closed and usually reduces the time needed to achieve such closure. In accordance with the present invention, a barrier or other mechanism is provided at a distal end of the hydratable hemostatic implant to function cooperatively with the retractable, protectable sleeve to keep the material of the implant dry and limit or prevent exposure to blood and other body fluids present in the tissue tract. A preferred form of such a distal seal will be a soluble plug, usually a soluble biopolymer which is biodegradable and resorbable within the tissue tract, preferably comprising hyaluronic acid (HA). While such soluble, bioresorbable plugs are particularly preferred, other mechanical barriers and sealing mechanisms could alternatively be employed so long as the mechanisms either comprise bioabsorbable materials or are coupled to the occlusion apparatus so that they are removed from the tissue tract together with other system components.

Apparatus according to the present invention for sealing a blood vessel wall penetration disposed at an end of a tissue tract comprise a shaft, a hydratable hemostatic implant, a protective sleeve, and an element or component which inhibits leakage of fluids beneath the protective sleeve which leakage can partially hydrate the hemostatic implant prior to retraction of the protective sleeve. The shaft has a proximal and distal end and is adapted to be introduced through the tissue tract so that the shaft distal end can be positioned within the blood vessel lumen. Usually, the shaft will be adapted so that it can be introduced through the vascular access sheath which is in place after performance of the interventional procedure.

Optionally, the device will further include an occlusion element disposed at or near the distal end of the shaft where the occlusion element is configured so that it may be shifted between a radially contracted configuration which facilitates introduction through the tissue tract and a radially expanded configuration for deployment within the blood vessel to occlude the penetration and provide temporary hemostasis. The hemostatic element could be a balloon or other inflatable structure, but will more usually be an expansible braid, coil, or other element which may be radially expanded by axial foreshortening. Typically, the shaft comprises an outer tube and an inner rod where a distal end of the occlusion element is attached to a distal end of the rod and a proximal end of the occlusion element is attached to a distal end of the outer tube. Thus, the occlusion element can be expanded and contracted by retracting and advancing the rod relative to the tube, respectively. The preferred occlusion element comprises a braided mesh covered with an elastic membrane. As described thus far, the shaft and occlusion element may be similar or identical to those described in the earlier referenced commonly owned patent applications.

The hydratable hemostatic implant of the present invention is disposed over an exterior surface of the shaft proximal to the occlusion element. The protective sleeve is retractably disposed over the hemostatic implant to protect it while the shaft is being introduced to the tissue tract. The hemostatic implant will typically comprise a body or wrapped sheet of hydratable, swellable material which partially or fully circumscribes the shaft, but other configurations could also be utilized. In a first embodiment, the hemostatic implant comprises a cylindrical body which is coaxially mounted about the shaft of the delivery device. Such fully circumscribing implants, however, can have difficulty being released from the shaft after they are exposed and hydrated. Thus, it will often be preferable to provide hemostatic implant configurations where the body partially circumscribes the shaft or is disposed in parallel to the shaft. When the implant is not disposed about the shaft, release upon rehydration will be greatly simplified as the rehydrated implant will lie adjacent to the shaft, allowing the shaft and the collapsed occlusion element to be drawn proximally past the rehydrated hemostatic implant with minimum interference. The hemostatic implant typically comprises a swellable, biodegradable polymer which swells upon hydration. Hydration is prevented when the polymer is introduced by the protective sleeve and the leakage-inhibiting component or element. The polymer hydrates and swells when the sleeve is retracted within the tissue tract, exposing the polymer to the body fluids. Suitable polymers include biodegradable hydrogels such as polyethylene glycols, collagens, gelatins, and the like.

The component or element which inhibits leakage of blood and other body fluids beneath the protective sleeve will preferably be a plug or mass of a biocompatiable, biodegradable material, such as a biopolymer, typically being a hyaluronic acid or other biopolymer which is able to block the blood or other body fluid from reaching the hydratable, swellable hemostatic implant and which will become fully hydrated and dissolve shortly after the protective sleeve is retracted from over the hemostatic implant.

An anti-proliferative agent may also be distributed within or otherwise carried by the material of the hemostatic implant. As most anti-proliferative agents, such as sirolimus, paclitaxel, and the like, are hydrophobic, it will usually be desirable to incorporate the anti-proliferative agents in a carrier, such as a biodegradable polymer, such a polylactic acid (PLA), poly(lactide-co-glycolide), and the like. The anti-proliferative agents may be incorporated into pores of polymeric beads or other structures which are dispersed or distributed within the biodegradable hydrogel or other swellable polymer. In certain embodiments, the anti-proliferative agents may be incorporated into nanoparticles, typically having dimensions in the range from 10 nm to 100 μm.

Agents useful as coagulation promoters, such as thrombin, tissue factors, components of the clotting cascade, and the like may also be incorporated into the body of the hemostatic implant. In some instances, it may be desirable to incorporate such coagulantion promoters into particulate or other carriers as described above with regard to the anti-proliferative agents.

In addition to the anti-proliferative agents and the coagulantion promoters, the hemostatic implants of the present invention may further incorporate radiopaque materials in or on at least a portion of the implant body. For example, a radiopaque material, such as barium, may be incorporated into the polymer, either by dispersion or chemical bonding. Alternatively, radiopaque rings, markers, and other elements, may be attached on or to the hemostatic implant, for example at each end of the implant to facilitate visualization of the implant as it is being implanted. Additionally or alternatively, radiopaque markers may be provided on the tube or shaft which carries the hemostatic implant so that the marker(s) align with a portion of the implant, typically either or both ends of the implant, prior to deployment.

In a preferred aspect of the present invention, the protective sleeve is held in place by a latch mechanism while it is being introduced. A separate key element is provided to release the latch mechanism and permit retraction of the sleeve after the device has been properly placed through the tissue tract and into the target blood vessel. The latch will be disposed on the shaft and will engage the protective sleeve to immobilize the sleeve during introduction. The key, which is usually slidably disposed on the shaft proximal of the latch, is able to shift the latch between a locking configuration where the sleeve is immobilized and an open configuration which allows the sleeve to be proximally retracted. Usually, the latch is spring-loaded to deflect radially outwardly from the shaft in a manner which engages the sleeve. The key is then adapted to radially depress the latch to release the sleeve. In a preferred embodiment, the latch and key mechanism will extend over a distal portion of the shaft having a length sufficient to allow manual access to the key latch even when the shaft is placed in the tissue tract.

In a further preferred aspect of the present invention, a backstop structure is provided on the shaft to engage the hemostatic implant to immobilize the implant while the sleeve is being proximally retracted. The backstop usually comprises a tube disposed on or coaxially over the shaft and having a distal end which engages a proximal end of the hemostatic implant. The backstop engages the hemostatic implant to prevent accidental dislodgement while the occlusion element is being proximally retracted through the implant. The backstop may include a space or receptacle for receiving the retracted occlusion element, allowing the backstop to be held in place until the occlusion element has been fully retracted through the hemostatic implant.

The protective sleeve of the present invention may comprise an outer sleeve and a separately retractable inner release sheath. The outer sleeve and inner release sheath are usually mounted coaxially so that the outer sleeve may be retracted over the inner release sheath while the inner release sheath remains stationary over the implant and acts as a friction barrier between the outer sleeve and implant. Without the inner release sheath, the protective sleeve, which applies the compressive and constrictive forces to the hemostatic implant, could stick to the hemostatic implant and make retraction of the protective sleeve and deployment of the implant difficult. The inner release sheath is preferably axially split so that, once the outer sleeve is retracted, the inner release sheath opens to release the implant and facilitate retraction of the release sheath. In preferred embodiments, the outer sleeve can engage the inner release sheath after the outer sleeve has been partly retracted. During the remainder of the outer sleeve retraction, the outer sleeve will then couple to and retract the inner release sheath to fully release the hemostatic implant. In addition to the use of the inner release sheath, the distal end of the protective sleeve may be sealed with a biodegradable substance, such as a glycerin gel, which can inhibit premature hydration of the hemostatic implant prior to release.

In a further preferred aspect of the present invention, the key of the latch mechanism can include a coupling element which attaches to the protective sleeve as the key is advanced and the latch is released. After the key couples to the protective sleeve, the key can be used to retract the protective sleeve. That is, rather than having to separately retract both the key and the protective sleeve, only the key needs to be retracted.

Methods according to the present invention for sealing a blood vessel penetration disposed at the end of a tissue tract comprise providing an apparatus including a shaft, a hydratable hemostatic implant disposed on an exterior surface of the shaft, and an element or component for inhibiting leakage of fluids beneath the protective sleeve. The shaft is introduced through the tissue tract to position the occlusion element in the lumen of the blood vessel and the hemostatic implant within the tissue tract. The hydratable hemostatic implant is covered by a protective sleeve while the shaft is being introduced through the tissue tract, and an occlusion element is optionally deployed to temporarily inhibit blood flow from the blood vessel into the tissue tract. The protective sleeve is then retracted to expose the hemostatic implant, where the implant typically absorbs fluid and expands to provide the desired seal within the tissue tract. Prior to retraction of the protective sleeve, the element or component for inhibiting leakage of fluids inhibits or prevents fluid from leaking beneath the protective sleeve and prematurely hydrating a portion of the hydratable hemostatic implant. As discussed above, such premature hydration of the material of the hydrostatic implant not only makes retraction of the sleeve more difficult, it can also result in an uneven (asymmetric) swelling of the implant which can interfere with full occlusion when the implant is deployed in the tissue tract. The preferred materials and types of leakage-inhibiting elements and components are discussed above in connection with the apparatus of the present invention.

After the hemostatic implant has expanded sufficiently, the occlusion element will be collapsed, and the shaft and collapsed occlusion element withdrawn leaving the hemostatic implant in the tissue tract. As described above, it will usually be preferred to position the hemostatic implant laterally or to the side of the shaft which carries the occlusion element. By thus positioning the occlusion element to bypass the hydrated hemostatic implant, withdrawal of the collapsed occlusion element past the hydrated hemostatic implant can be greatly facilitated. Preferably, the material of the hemostatic implant will degrade over time, preferably over a period of less than one year, more preferably over a period of less than six months, usually less than three months, leaving no material behind at the vascular access point.

In a preferred aspect of the methods of the present invention, the protective sleeve is latched to the shaft while the shaft is introduced. By "latched" is meant that the sleeve will be fixed or immobilized to the shaft by some mechanical link, where the link may be selectively disconnected or "unlatched" when it is desired to retract the sleeve and expose the hemostatic implant. Thus, the methods of the present invention will preferably further comprise unlatching the sleeve before retracting the sleeve. In a specific embodiment, the unlatching comprises distally advancing a key over the latch to effect the desired unlatching. As described above in connection with the apparatus of the present invention, an exemplary latch and key comprises a spring-like element which is secured over an exterior portion of the shaft. The spring-like element typically projects radially outward from the shaft when unconstrained. In this way, the spring-like latch element can engage the protective sleeve to prevent proximal retraction of the sleeve. The latch can be released by advancing a cylindrical or other key element distally over the shaft to depress the spring-like lock element.

In a further preferred aspect of the method of the present invention, a proximal portion of the sleeve will be configured to lie proximal to, i.e., outside of, the tissue tract when the occlusion element is deployed in the blood vessel lumen. Usually, the key element will lie further proximal of the sleeve, permitting the user to manually deploy the key to unlock the latch and to further manually retract the protective sleeve by manually clasping an exposed portion of the sleeve and pulling it proximally from the tissue tract. Typically, the sleeve will have a length in the range from 2 cm to 30 cm, more typically from 5 cm to 15 cm.

In a still further preferred aspect of the method, the hemostatic implant will be constrained to prevent it from being displaced proximally while the shaft is being introduced through the tissue tract. In particular, the backstop or other element may be fixed to the shaft in a location selected to engage the hemostatic implant or an extension thereof to prevent the implant from being displaced proximally, either as the shaft is being introduced or more likely as the protective sleeve is being proximally retracted over the implant. Usually, the backstop or other element will be slidably mounted over the shaft so that it may be held in place as the occlusion element is retracted past the hemostatic implant.

In a specific aspect of the method of the present invention, radiopaque markers on or within the shaft or hemostatic implant are used to verify the location of implant prior to release. Inclusion of radiopaque markers on the delivery shaft is particularly useful when no radiopaque material is incorporated within the hemostatic implant. Preferably, there will be at least two distinct radiopaque bands, with one at each end of the implant. By observing the orientation of the two markers, the physician can determine whether the implant is properly aligned adjacent to the vascular penetration or has inadvertently advanced into a lumen of the blood vessel prior to deployment. In particular, by measuring or visually assessing the apparent distance between the bands when the device is being fluoroscopically imaged from an anterior aspect, the apparent distance between the bands will be longer if the hemostatic implant is within the blood vessel lumen than if it is within the tissue tract immediately above the blood vessel wall penetration. Such apparent differences in the positions of the two radiopaque marker bands results from the foreshortening of the vertical angle at the entry through the wall penetration into the blood vessel lumen. For example, if the tissue tract is disposed at a 45° angle with respect to the horizontal orientation of the blood vessel lumen, in an anterior view, the marker bands will appear to be approximately 30% closer to each other than they would in the horizontal view when they are present in the blood vessel lumen.

DETAILED DESCRIPTION OF THE INVENTION

Figure 1:
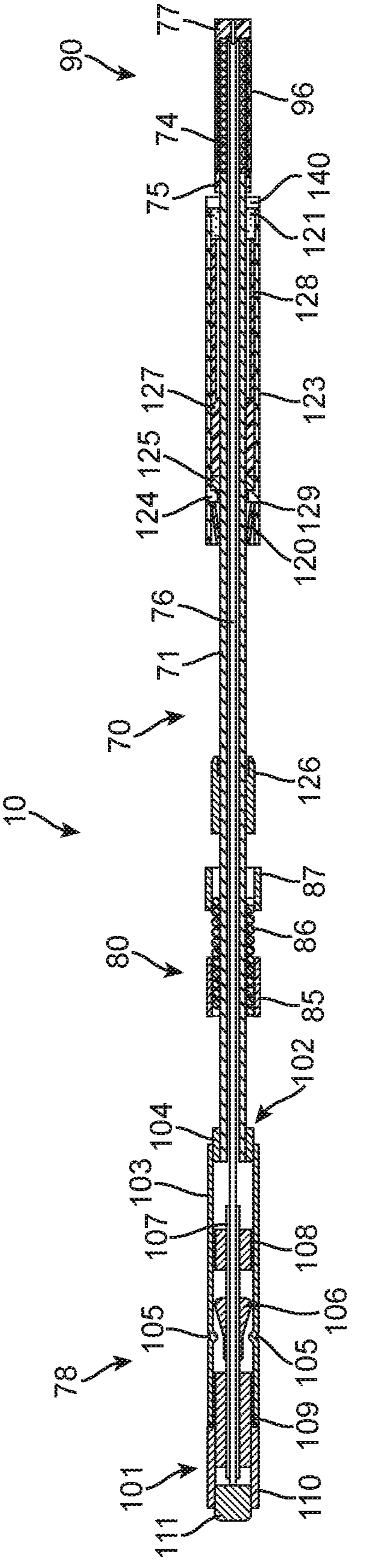
FIG. 1 illustrates an exemplary sealing apparatus constructed in accordance with the principles of the present invention, shown in section.
Figure 1A:
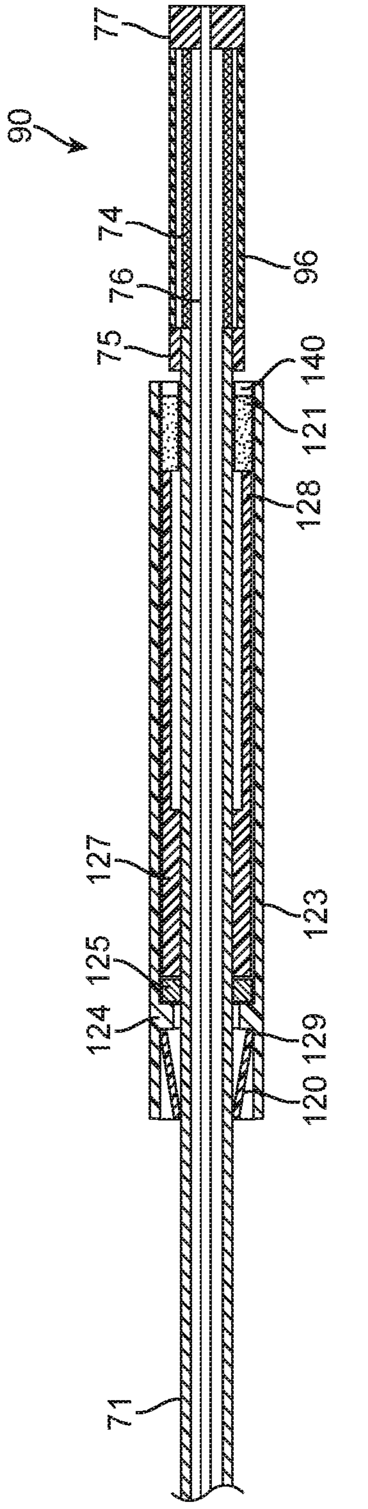
FIG. 1A is a detailed view of a distal portion of the sealing apparatus of FIG. 1, shown in partial section.

Referring to FIGS. 1 and 1A, an exemplary sealing apparatus 10 constructed in accordance with the principles of the present invention comprises a shaft assembly 70 including an outer tube 71 and an inner rod 76. An expansible occlusion element 90 is mounted at a distal end (to the right in FIGS. 1 and 1A) of the shaft assembly 70 and includes a radially expansible mesh 74 covered by an elastomeric membrane 96. A handle assembly 78 is attached to a proximal end of the shaft assembly 70 and is operatively attached to both the outer tube 71 and inner rod 76 so that the inner rod can be axially advanced and retracted relative to the outer tube. The inner rod 76 and outer tube 71 are coupled together at the distal tip of the sealing apparatus 10 by a plug 77 and a proximal anchor 75, respectively. The occlusion element 90 is held between the plug 77 and the proximal anchor 75 so that axial retraction of the rod in the proximal direction (to the left as shown in FIGS. 1 and 1A) foreshortens the occlusion element 90, causing the occlusion element to expand radially, as shown for example in FIG. 2.

Figure 2:
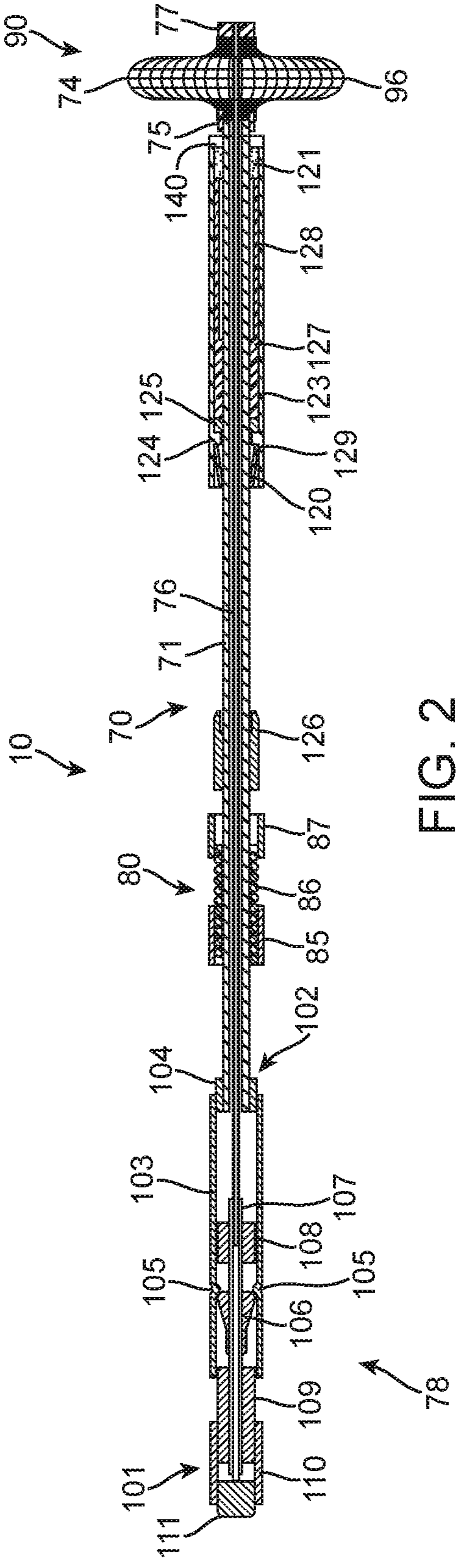
FIG. 2 is a cross-sectional view of the sealing apparatus of FIG. 1, shown with an expanded occlusion element.

Axial advancement and retraction of the rod 76 relative to the outer tube 71 is effected using the handle assembly 78. The handle assembly 78 includes a cylindrical body 103 attached to the proximal end of the outer tube 71 by a bushing 104 so that the body 103 will remain fixed relative to the outer tube as the inner rod 76 is retracted and advanced. The inner rod is retracted and advanced by a slide assembly 101 which includes a short tube 110 fixedly attached to an endcap 111 and a slide cylinder 109. The inner rod 76 is secured by tube element 107 which carries locking element 106 and bearing elements 108 and 109. Bearing element 109 is attached to proximal grip 101 and the assembly of the grip 101 and tube element 107 can slide freely within the interior of the cylindrical body 103 so that the rod 76 may be proximally retracted relative to the body 103 and outer tube 71, as shown in FIG. 2. Once the expansible occlusion element 90 has been radially expanded, the rod 76 will remain retracted and is held in place by locking element 106 which is pulled over a detent 105, again as shown in FIG. 2. An alignment bushing 108 is provided in the interior of the cylindrical body 103 to maintain alignment of the slide assembly 101 relative to the cylindrical body.

The sealing apparatus of the present invention may optionally include a tensioning mechanism 80 which includes a coil spring 86. a gripping element 85, and a coupling element 87. The tensioning mechanism 80 may be selectively positioned along the length of shaft assembly 70, and will provide a tension determined by the constant of coil spring 86 to hold the expanded occlusion element 74 against the vascular penetration, as described in more detail in copending, commonly-owned application Ser. No. 10/974,008, the full disclosure of which is incorporated herein by reference. As described thus far, the construction and use of the sealing apparatus including shaft assembly 70, handle assembly 78, tensioning mechanism 80, and expansible occlusion element 90 are generally the same as illustrated in copending application Ser. No. 10/974,008. The present invention is directed at modifications and improvements to the earlier device for delivering a hemostatic implant into the tissue tract generally above the vascular wall penetration, as will be described in more detail below.

As best seen in FIG. 1A, a hydratable hemostatic implant 121, which will typically be a biodegradable polymer as described in more detail above, is carried coaxially or in parallel over the outer tube 71 near the distal end thereof proximal to the expansible occlusion element 90. While the hydratable hemostatic implant 121 is shown to be positioned coaxially over outer tube 71 in FIG. 1A, it will often be desirable to modify or reposition the implant in order to facilitate release from the sealing apparatus after the implant has been deployed. More simply, the hemostatic implant could be axially split to allow it to partially open after it is rehydrated and facilitate passage of the collapsed occlusion element 74 as the sealing apparatus is being withdrawn. Alternatively, the hemostatic implant may be reconfigured and carried laterally (i.e., to one side of) with respect to the shaft of the sealing apparatus, as described in more detail hereinafter with respect to FIGS. 9A and 9C. The hydratable hemostatic implant 121 could alternatively be carried on the inner surface of a protective sleeve 123 which is slidably carried over the outer tube 71. The protective sleeve 123 slides over a backstop 127 which is slidably mounted over the outer tube 71 and which is prevented from moving proximally by stop member 125 which is fixed to the outer surface of the outer tube. Backstop 127 has a distal end 128 which engages a proximal end of the hemostatic implant 121. Thus, by proximally retracting the protective sleeve 123, the hydratable hemostatic implant 121 can be exposed to the tissue tract and released from the sealing apparatus. Prior to retraction of the protective sleeve 123, a biodegradable plug 140 protects the hydratable hemostatic implant 121 from exposure to blood or other body fluids when present in the tissue tract. The plug 140 may be composed of any of the materials discussed above, typically being formed from hyaluronic acid which is highly water soluble. So long as the hyaluronic acid plug 140 remains beneath the protective sleeve, it will retain sufficient mechanical integrity to block or inhibit passage of significant amounts of fluids to the hydratable hemostatic implant 121. Once the protective sleeve 123 is retracted, however, the hyaluronic acid will quickly absorb water and dissolve in the body fluids, becoming resorbed by the tissue over a relatively short time frame. In contrast, the swollen collagen plug will not dissolve and will be resorbed only slowly over time in order to provide the desired hemostatic effect.

Accidental axial retraction of the protective sleeve 123 is prevented by a latch mechanism including a latch element 120 and a key 126 (FIGS. 1 and 2). The latch element 120 is typically a spring-loaded component, for example a conical spring having a narrow diameter end attached to the outer tube 71 and a flared or larger diameter end 129 which engages a stop ring 124 formed on the inner surface of the protective sleeve 123. So long as the flared end 129 of the latch element 120 remains in its flared or open configuration, as illustrated in FIG. 1A, accidental proximal retraction of the sleeve is prevented. It is further noted that the stop ring 124 engages stop member 125 of the backstop 127 preventing accidental distal movement of the protective sleeve 123. Thus, when the sealing apparatus 10 is introduced to a tissue tract, as described in more detail below, movement of the protective sleeve 123 in either the distal or proximal direction is inhibited.

Figure 3:
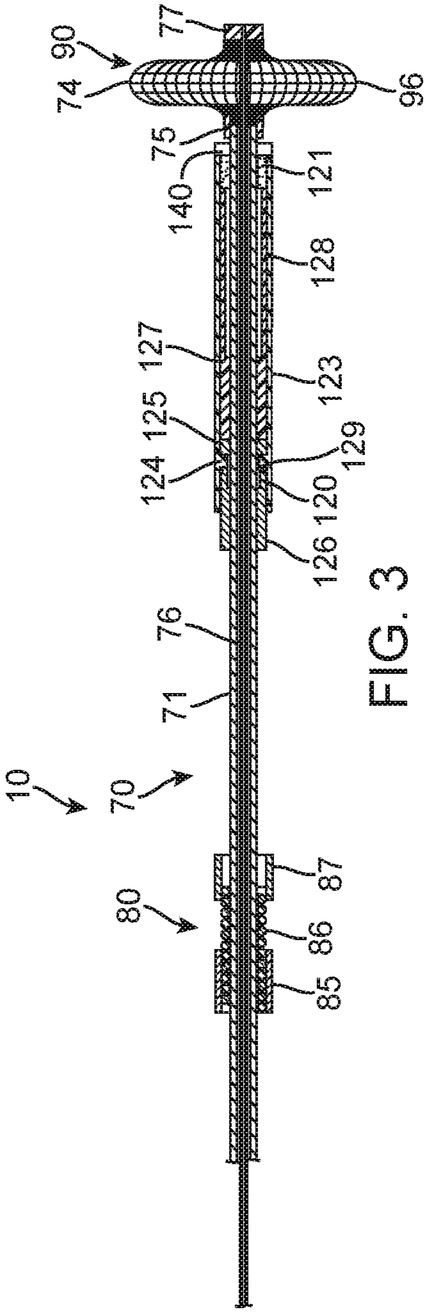
FIGS. 3-7 illustrate the further steps of deployment of the hemostatic implant from the apparatus of FIGS. 1 and 2.

To allow selective proximal retraction of the protective sleeve 123, the key 126 (FIGS. 1 and 2) may be axially advanced to engage the latching element 120, as illustrated in FIG. 3. The key 126 fits inside of the protective sleeve 123 and depresses or radially contracts the latch element 120 so that it fits within the interior circumference of the stop ring 124, thus allowing proximal retraction of the protective sleeve 123, as shown in FIG. 4.

Figure 4:
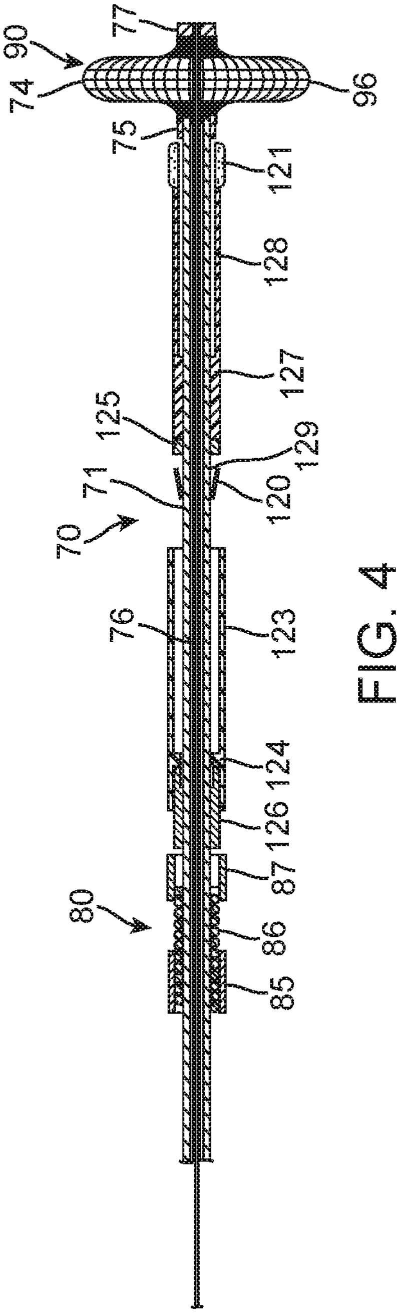
Figure 5:
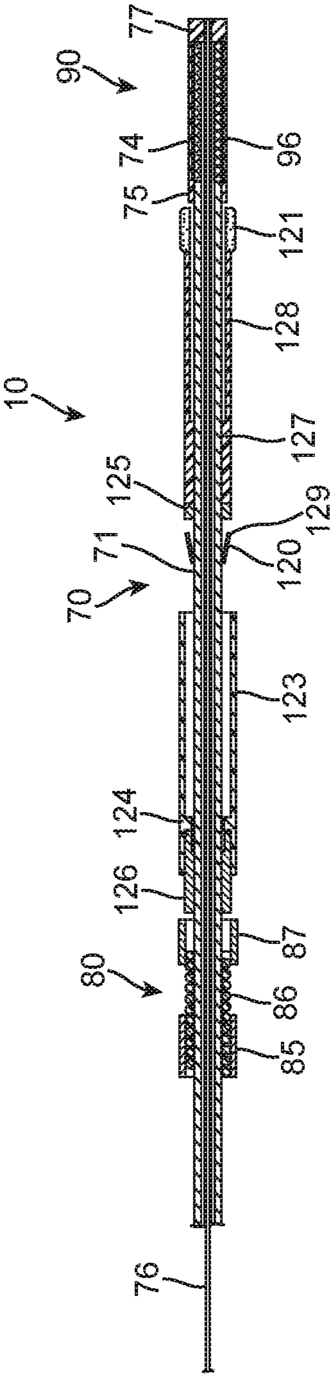
Figure 6:
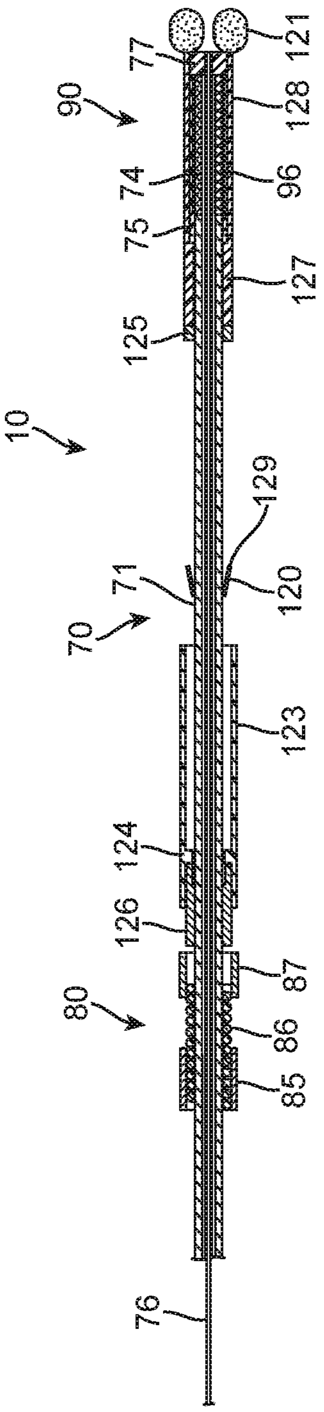
Figure 7:
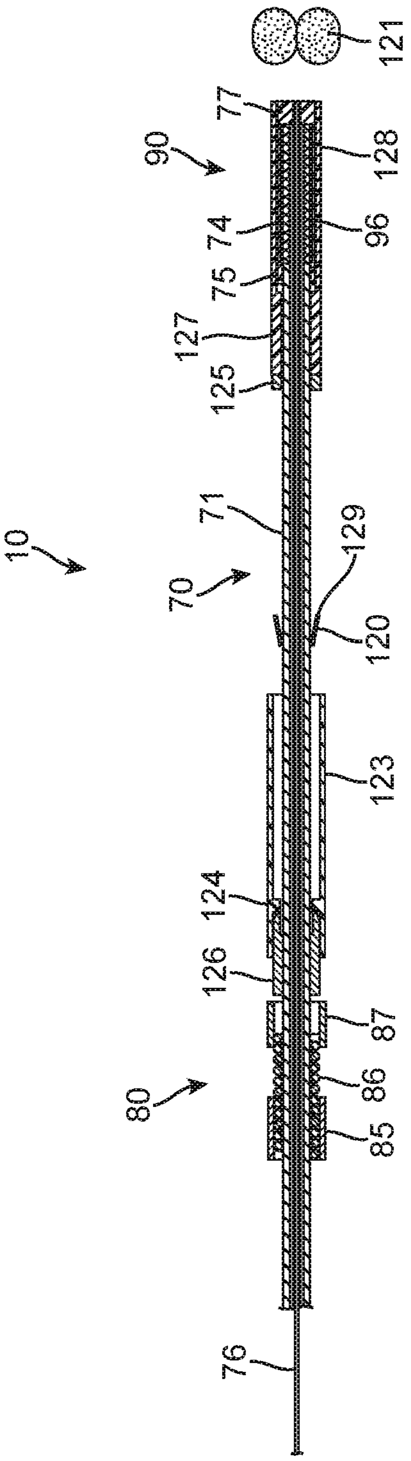

Once the key 126 has engaged and constrained the latch element 120, as shown in FIG. 3, the protective sleeve 123 may be proximally withdrawn past the hemostatic implant 121 and the backstop 127, as shown in FIG. 4. Thus, the hemostatic implant 121 will be released from constraint and exposed to the environment in the tissue tract. The environment in the tissue tract will include blood and other body fluids which can hydrate the hemostatic implant 121, causing swelling as shown in FIG. 4. The swelling will continue, as shown in FIG. 5, and the radially expanded occlusion element 90 can be collapsed using the handle assembly, as shown in FIG. 5. The collapsed occlusion element 90 can then be proximally withdrawn into and through the backstop assembly 127, as shown in FIG. 6 (where an annular space may be provided to accommodate the occlusion element). When the occlusion element has been fully withdrawn within the backstop 127, the hemostatic implant is completely released, as shown in FIG. 6, and the remaining portions of the sealing apparatus can be pulled away from the hemostatic implant, as shown in FIG. 7.

Figure 8B:
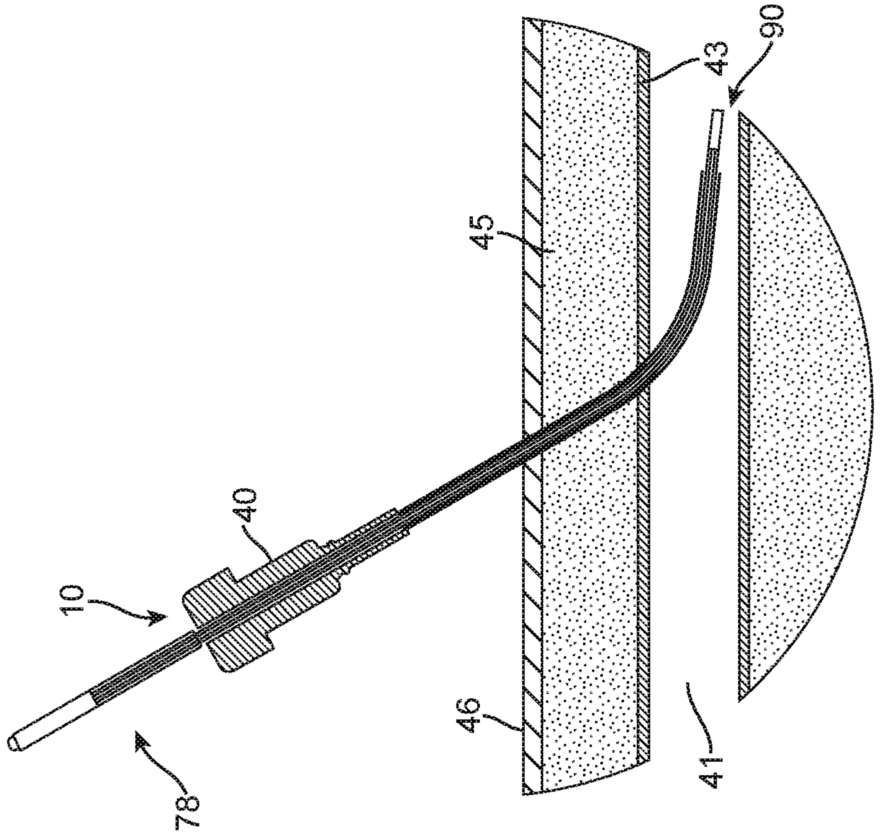
FIGS. 8A-8I illustrate placement and deployment of the hemostatic implant using the apparatus of FIGS. 1 and 2 through a vascular sheath placed in a blood vessel.
Figure 8A:
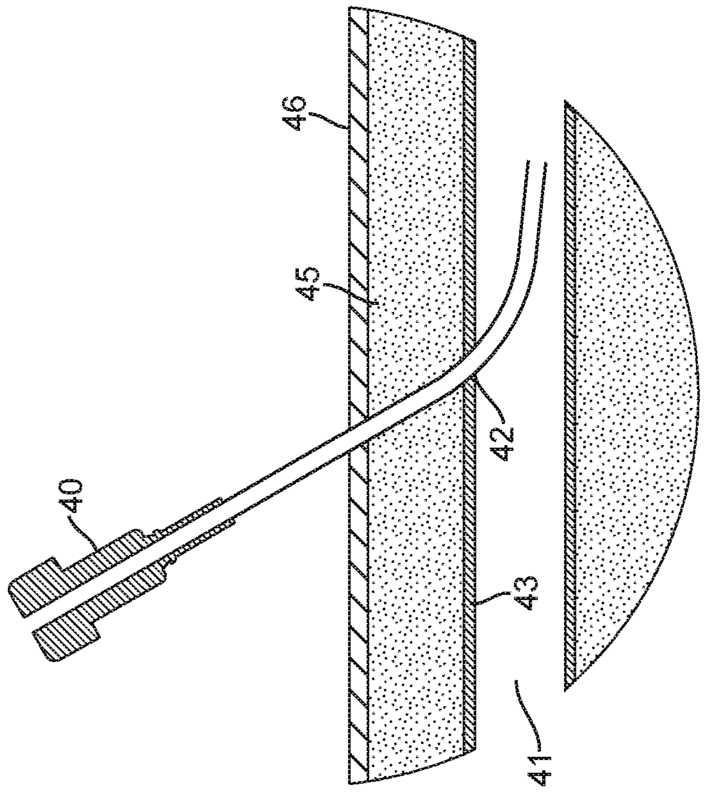
Figure 8D:
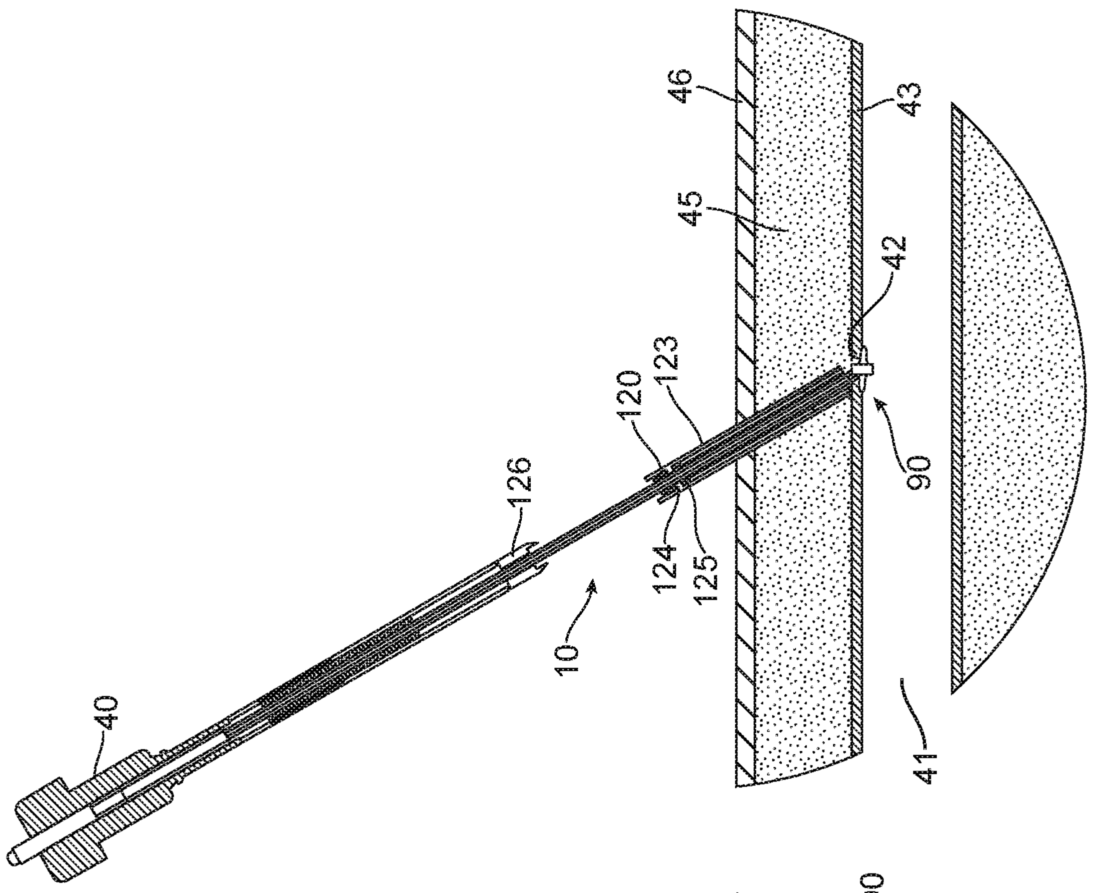
Figure 8C:
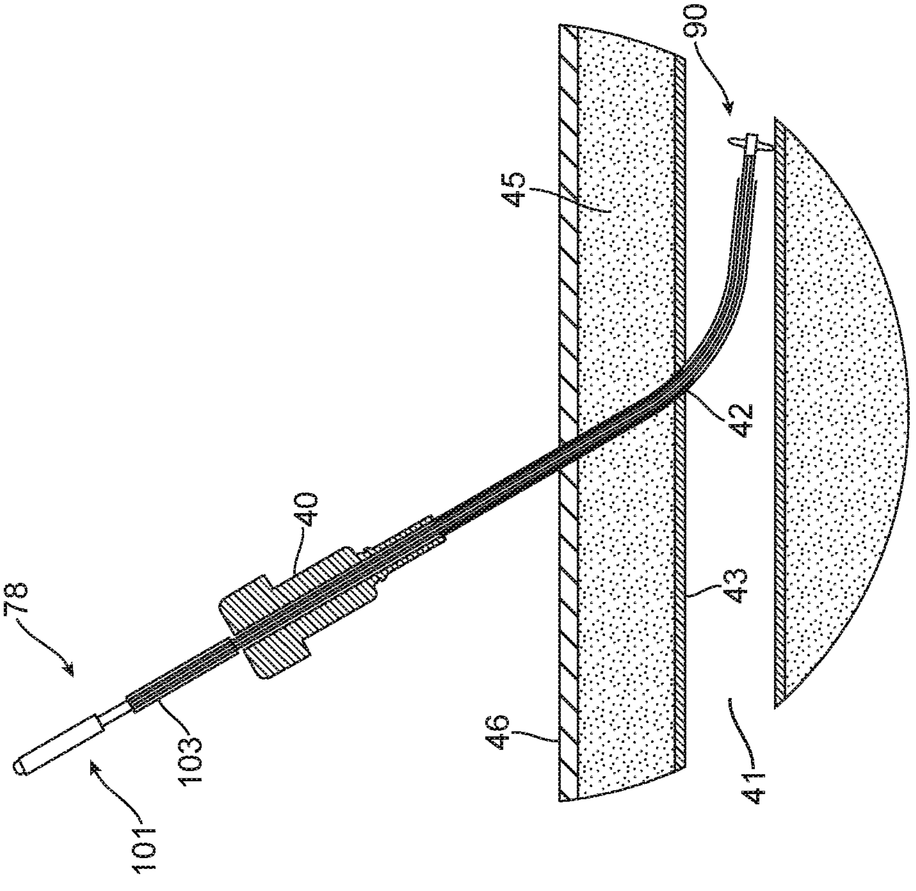

Referring now to FIGS. 8A-8I, deployment and use of the sealing apparatus 10 of the present invention through an introducer sheath 40 will be described in more detail. Introducer sheath 40 will typically be in place within a blood vessel lumen 41 passing from the skin surface 46 through tissue 45 in a tissue tract. A vascular wall penetration 42 will thus be present in the vascular wall 43, all as shown in FIG. 8A. The sealing apparatus 10 is then introduced through the access sheath 40 so that the expansible occlusion element 90 passes out through the distal end of the sheath, as shown in FIG. 8B. Handle assembly 78 will remain outside of the sheath and accessible to the user so that the slide assembly 101 may be pulled relative to the cylindrical body 103 to radially expand the occlusion element 90, as shown in FIG. 8C. The vascular access sheath 40 may then be withdrawn over the exterior of the sealing apparatus 10 while the sealing apparatus is simultaneously withdrawn to seat the expanded occlusion element 90 against the vascular penetration 42, as shown in FIG. 8D.

Figure 8F:
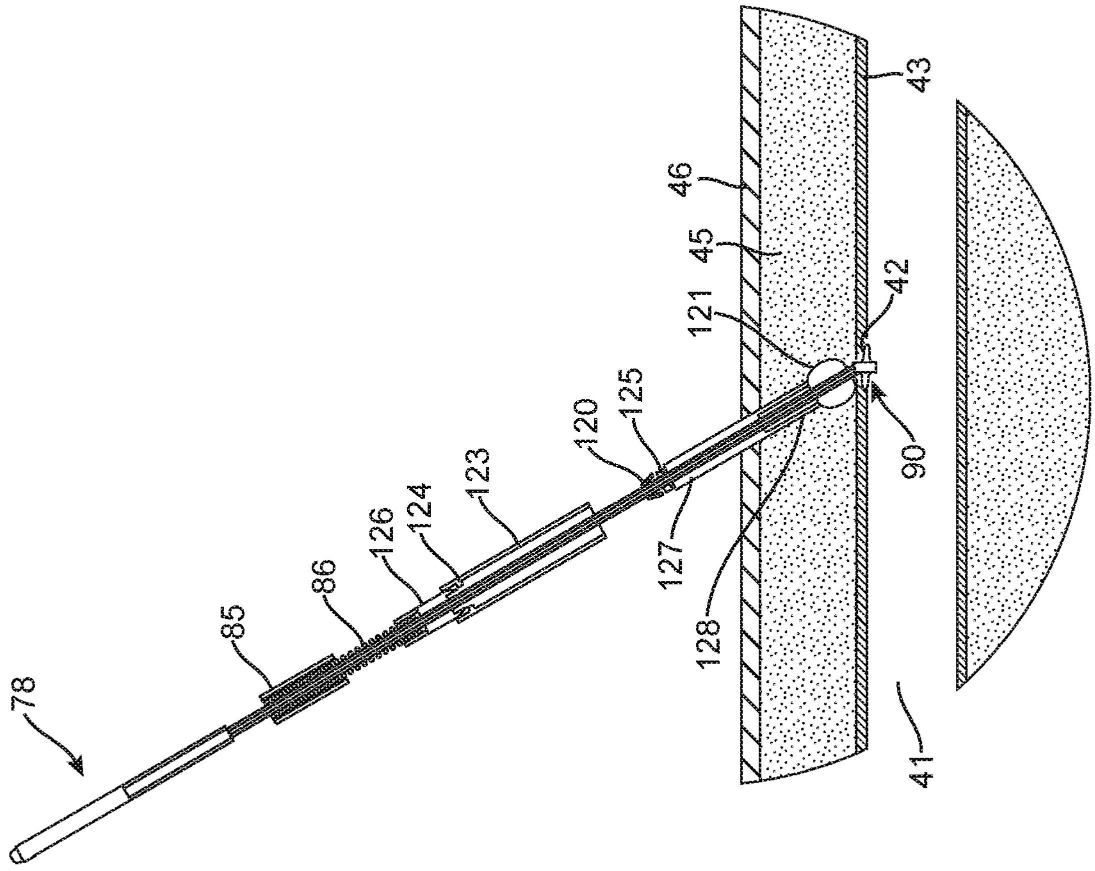
Figure 8E:
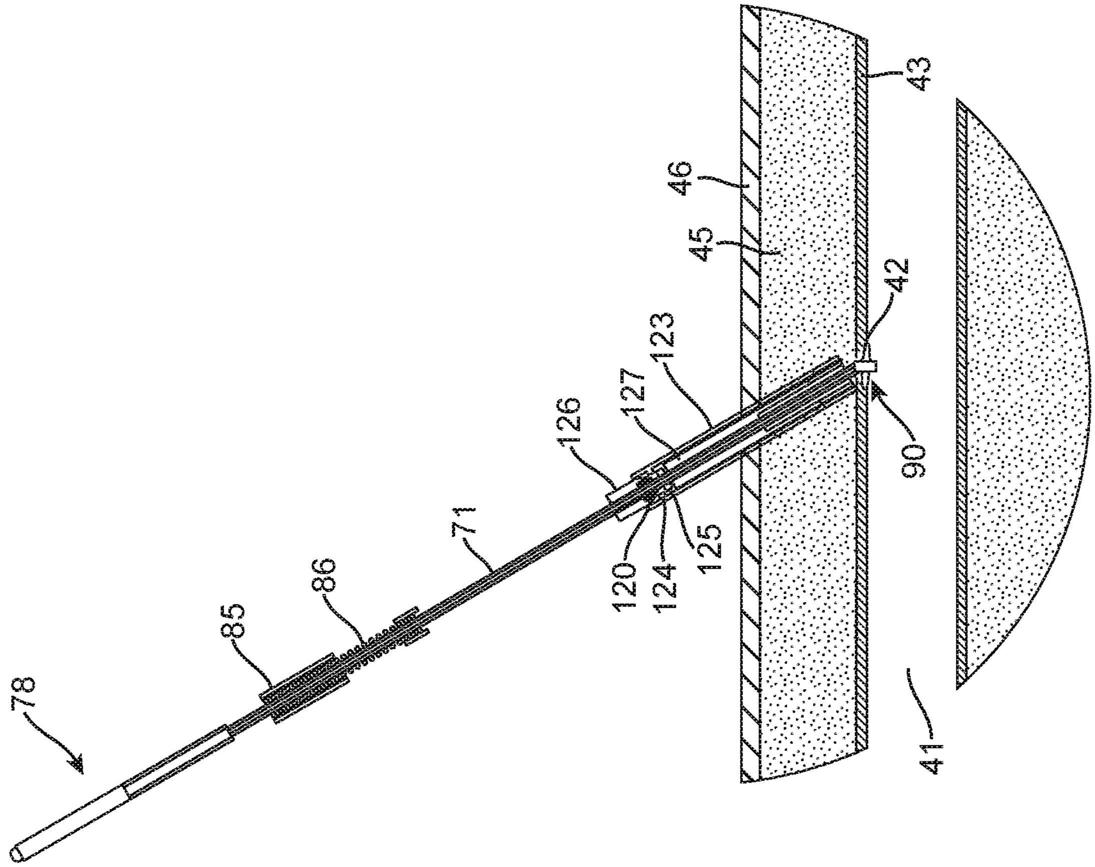
Figure 8H:
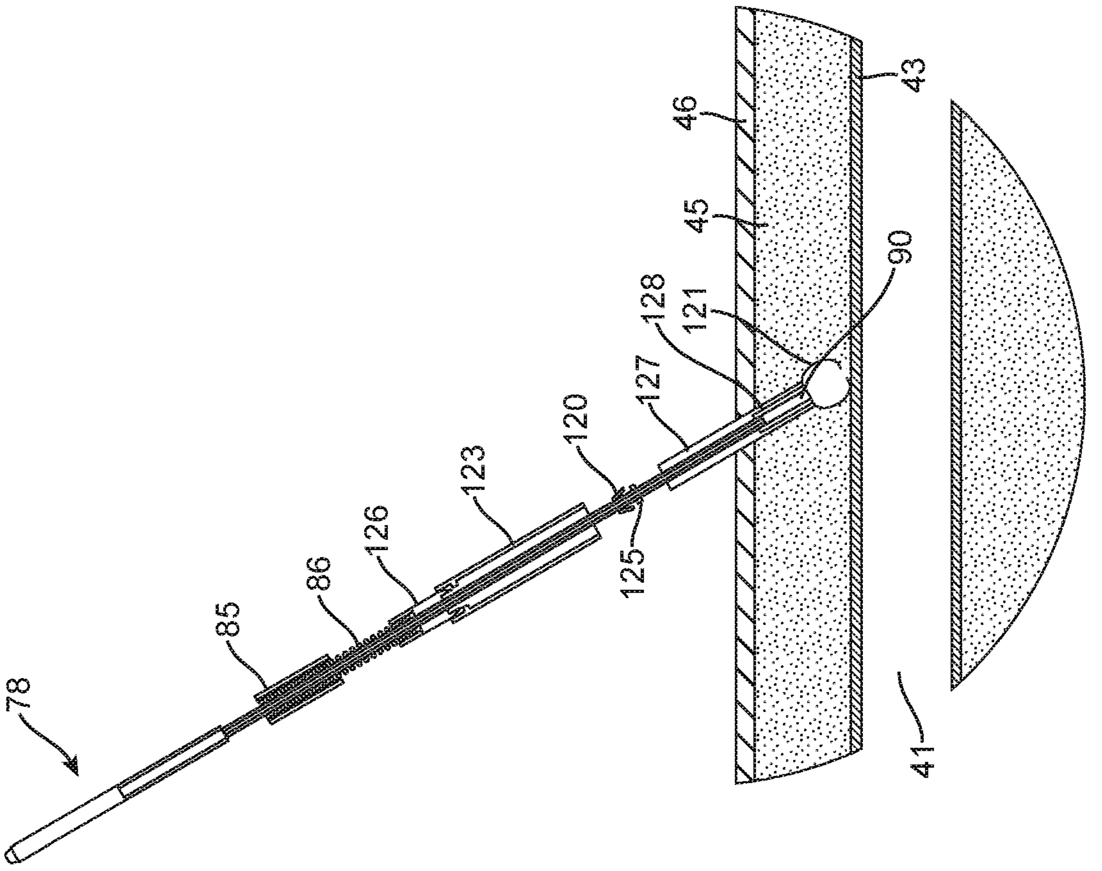
Figure 8G:
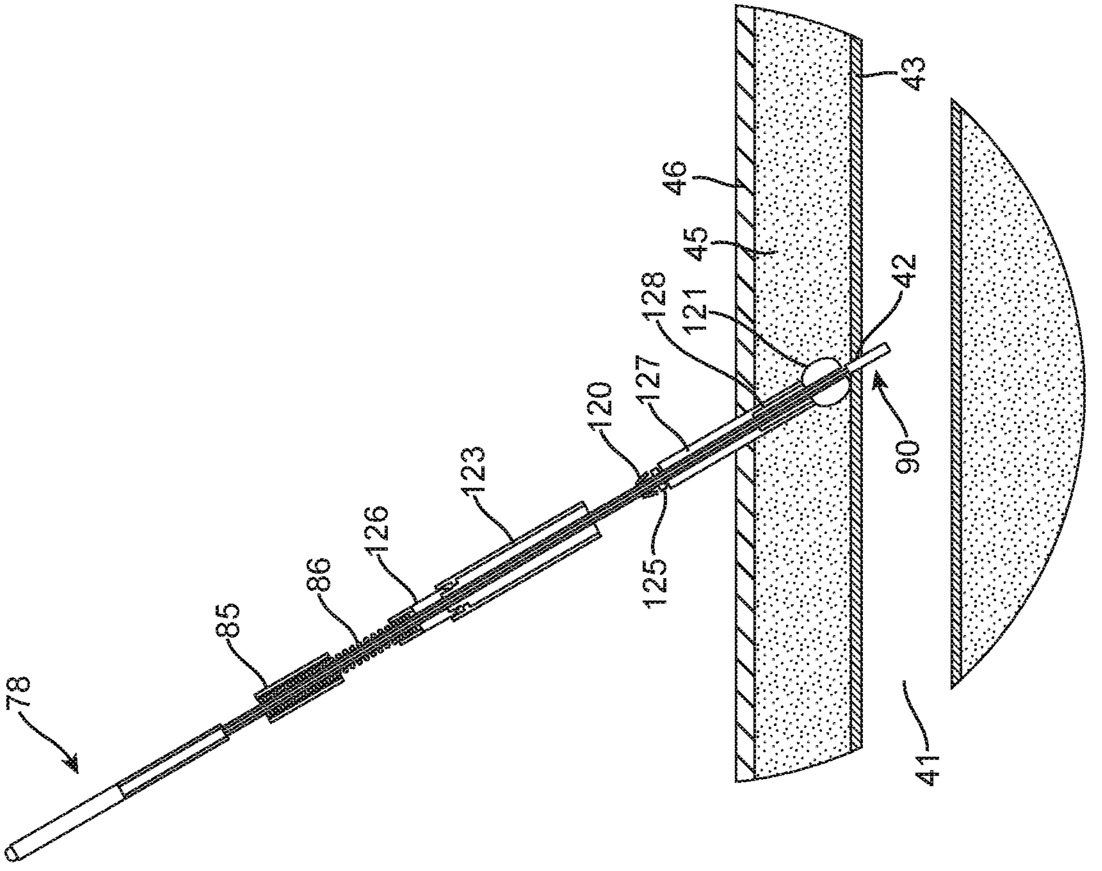
Figure 8I:
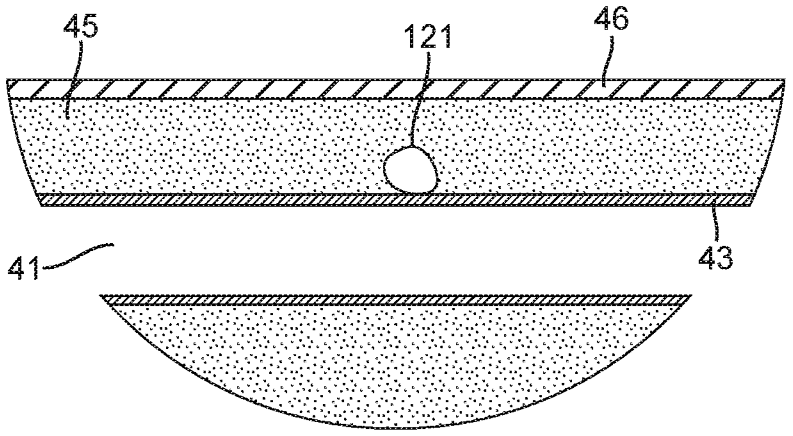

At that point, the protective sleeve 123 and key 126 become exposed and available to the user for manipulation. The key may then be distally advanced over the outer tube 71 so that the key engages and depresses the latch 120 (FIG. 1A) as illustrated in FIG. 8E. The key 126 and protective sleeve 123 may then be manually pulled in a proximal direction over the outer tube 71 to release the hemostatic implant 121, as shown in FIG. 8F. The expandable element 90 may then be collapsed, as shown in FIG. 8G, and the collapsed element withdrawn into the distal end of the sealing apparatus, as shown in FIG. 8H. The entire sealing apparatus 10, except for the hemostatic implant 121, may then be withdrawn from the tissue tract, leaving the hemostatic implant 121 in place over the now closed vascular wall penetration, as shown in FIG. 8I. The hemostatic implant, which may optionally carry the anti-proliferative, coagulation promoting, and/or radiopaque substances described above, will remain in place inhibiting bleeding through the upper portions of the tissue tract and allowing the vascular wall penetration to heal. Over time, the hemostatic implant 121 will preferably biodegrade, leaving a healed tissue tract and vascular wall penetration which are usually suitable for re-entry at a subsequent time.

Figure 9A:
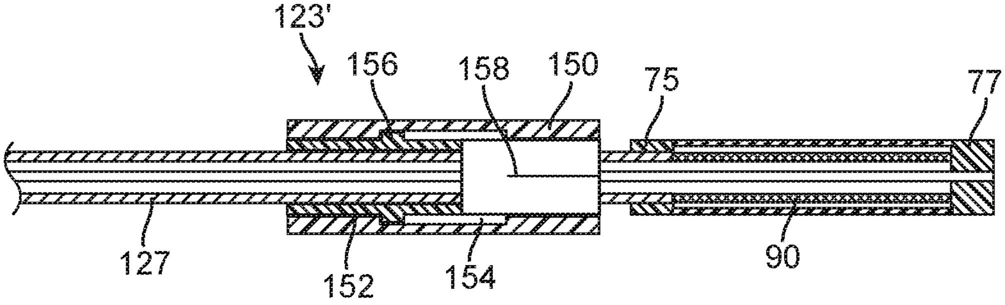
FIGS. 9A-9C illustrate a sealing apparatus in accordance with the present invention having a protective sleeve including an outer sleeve and an inner release sheath.
Figure 9B:
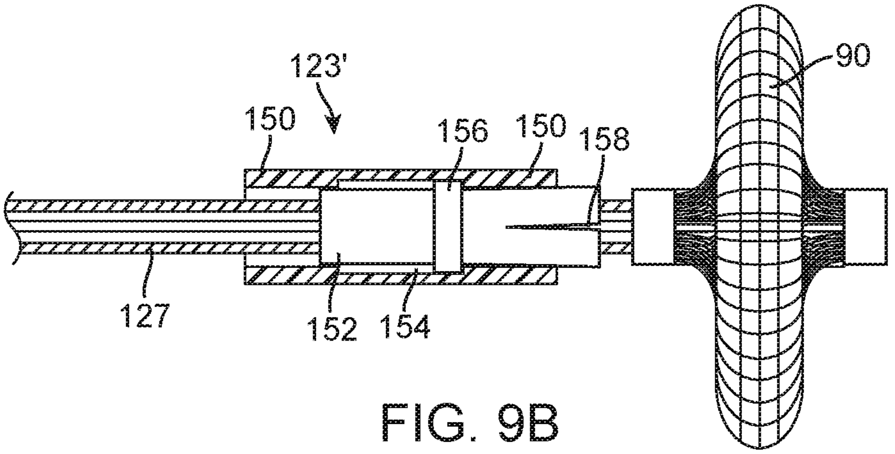
Figure 9C:
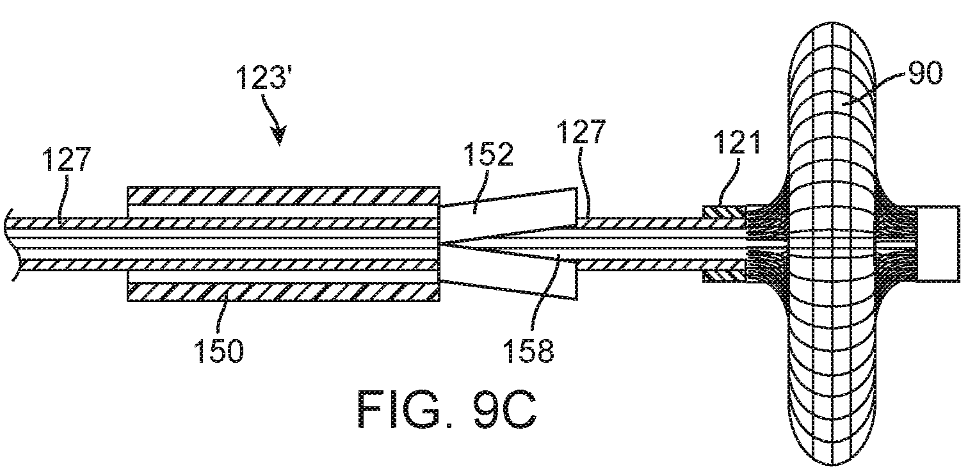

Referring now to FIGS. 9A-9C, a protective sleeve 123' comprises an outer sleeve 150 and an inner release sheath 152. The outer sleeve 150 and inner release sheath 152 are separately retractable so that the outer sleeve may first be retracted relative to the hemostatic implant 121 (FIG. 9C) while the inner release sheath initially remains over the implant. The release sheath 152 will thus provide an anti-friction interface so that the outer sleeve 150 slides over the implant 121 with reduced sticking. The inner release sheath 152 is preferably formed from a relatively lubricious or slippery material and will preferably include an axial opening or slit 158 which permits the distal portion thereof to partially open after the outer sleeve 150 has been retracted, as shown in FIG. 9B. Once the outer sleeve 150 has been retracted to relieve constraint over the hemostatic implant, the inner sleeve may then be retracted to completely release the hemostatic implant, as shown in FIG. 9C. Conveniently, the outer sleeve 150 may be coupled to the inner release sheath 152 so that proximal retraction of the outer sleeve will automatically retract the inner release sheath at the proper point in travel. For example, a cavity or channel 154 may be formed in an inner surface of the outer sleeve 150 and a ring or other engaging element 156 may be formed on the outer surface of the inner release sheath 152. Initially, the ring 156 will be positioned at the distal end of the cavity or channel 154, as shown in FIG. 9A. After the outer sleeve 150 has been retracted so that it no longer lies over the implant 121, the ring may then engage a distal end of the cavity or channel 154, as shown in FIG. 9B, and engage the ring 156, allowing the outer sleeve to then pull the inner sleeve proximally, as shown in FIG. 9C, to fully release the hemostatic implant 121.

Figure 10A:
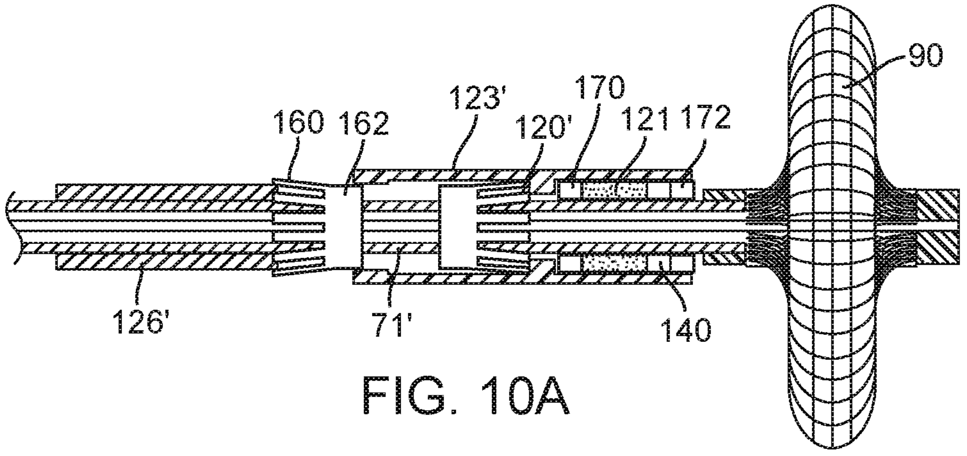
FIGS. 10A-10C illustrate a sealing apparatus in accordance with the present invention having a key latch mechanism which engages the protective sleeve and may be used to proximally withdraw the sleeve to deploy the hemostatic implant.
Figure 10B:
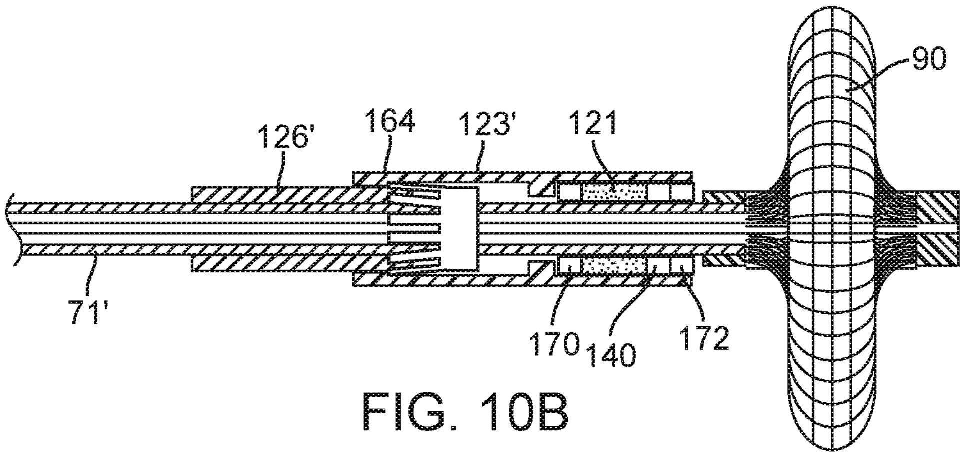
Figure 10C:
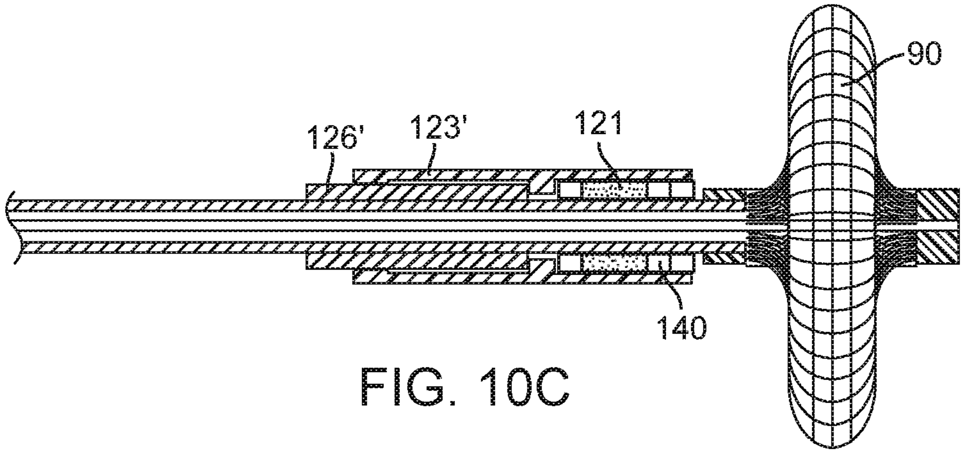

Referring now to FIGS. 10A-10C, it is also possible to selectively couple the key 126' to a protective sleeve 123'. The key 126' has a coupling element, such as plurality of proximally disposed barbs 160 at its distal end. The key 126' may be advanced into the protective sleeve 123' where a distal end 162 of the key 126' engages latching element 120' on the outer tube 71'. Latching mechanism 120' may conveniently comprise a plurality of barbs so that advancement of the key 123' radially closes the barbs along the protective sleeve 123' to be proximally retracted relative to the tube 71'. Once the key 126' is fully distally advanced, as shown in FIG. 10B, the proximally disposed barbs 160 will engage an inner lip 164 at the proximal end of the protective sleeve 123'. Thus, as the key 126' is proximally retracted, as shown in FIG. 10C, the key will pull the protective sleeve 123' in a proximal direction, thus exposing the implant 121 and dissolvable plug 140.

A further aspect of the present invention is illustrated in FIGS. 10A and 10B. Radiopaque marker bands 170 and 172 may be provided at the proximal and distal ends of the implant 121, respectively. Usually, these bands will be disposed on the outer tube 71', but they could also be disposed on or incorporated within the hemostatic implant 121. In either case, they are useful to evaluate positioning of the hemostatic implant prior to deployment, as described in more detail below in FIGS. 13A, 13B, 14A, and 14B.

Figure 11A:
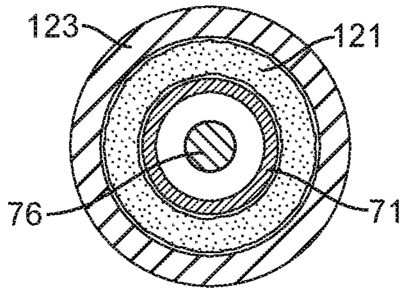
FIGS. 11A and 11B illustrate a hemostatic implant which is coaxially disposed about the shaft of the deployment apparatus of the present invention.
Figure 11B:
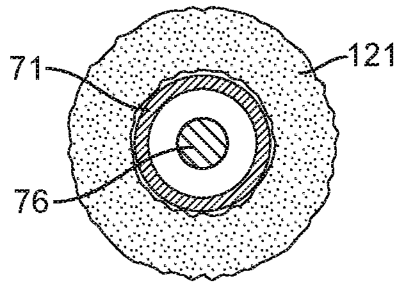

Referring now to FIGS. 11A and 11B, the hemostatic implant 121 may be disposed coaxially over the outer tube 71 and in a rod 76. By then proximally retracting the protective sleeve 123, the implant 121 is released and can hydrate as shown in FIG. 11B. As described previously, however, it will still be necessary to withdraw the outer tube 71 as well as the collapsed occlusion element 90 past the hemostatic implant 121. When the hemostatic implant 121 fully circumscribes the outer tube 71, however, both the tube 71 and the collapsed occlusion element 90 can tend to dislodge the implant within the tissue tract.

Figure 12A:
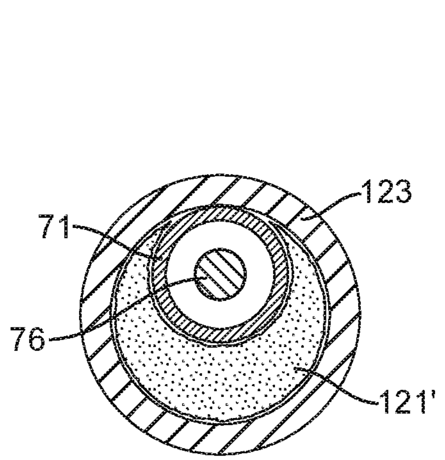
FIGS. 12A and 12B illustrate the hemostatic implant which is laterally disposed relative to the shaft of the deployment mechanism.
Figure 12B:
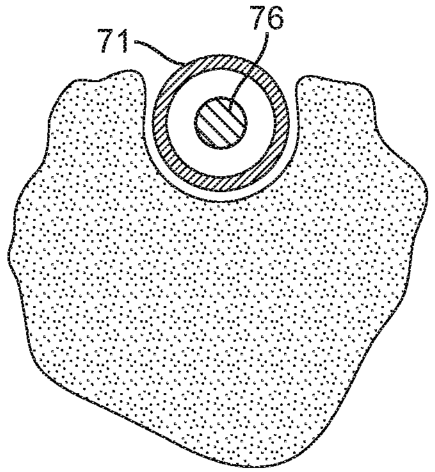

Therefore, in some instances, it will be desirable to modify the geometry of the implant to facilitate withdrawal of the outer tube and the collapsed occlusion element. For example, as shown in FIGS. 12A and 12B, hemostatic implant 121' can be formed with a crescent-shaped cross-section so that it does not fully circumscribe the outer tube 71 which carries it. By laterally displacing the outer tube 71 an inner rod 76 within the protective sleeve 123, as shown in FIG. 12A, the volume of the hemostatic implant 121 will be generally the same as that shown in FIG. 11A. When the protective sleeve 123 is withdrawn, however, as shown in FIG. 12B, the hemostatic implant 121 will hydrate and expand laterally on one side of the outer tube 71, as shown in FIG. 12B. By disposing the outer tube 71 and collapsed occlusive element 90 to one side of the implant, it is much easier to withdraw the apparatus and collapsed occlusion member past the implant without dislodging the implant within the tissue track.

Figure 13A:
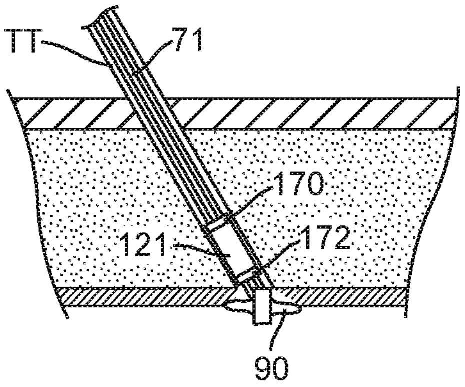
FIGS. 13A and 13B illustrate how aligned radiopaque markers may be utilized to determine that the hemostatic implant is properly located prior to deployment.
Figure 13B:
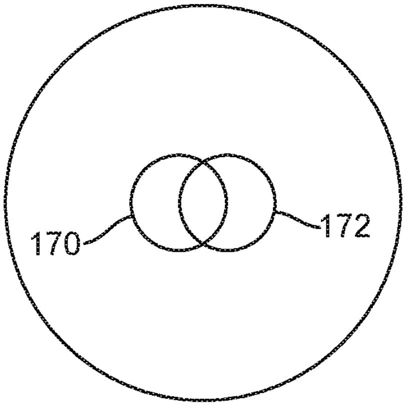
Figure 14A:
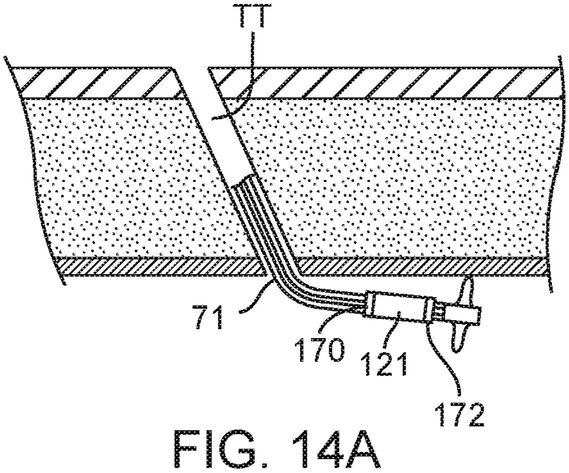
FIGS. 14A and 14B illustrate how such radiopaque markers would appear when the hemostatic implant is improperly positioned prior to deployment.
Figure 14B:
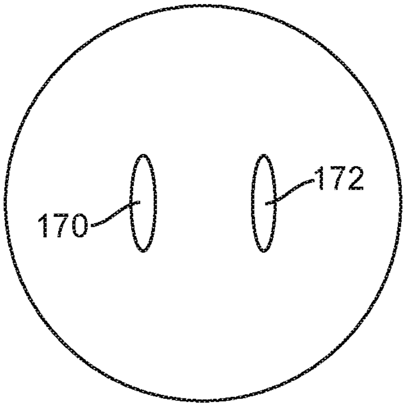

Referring now to FIGS. 13A and 13B, the radiopaque markers 170 and 172 can be used to determine whether the hemostatic implant 121 is oriented properly prior to deployment. For simplicity, the protective sleeve and other components of the deployment system are not shown in FIGS. 13A and 13B (or in 14A and 14B as described below). The radiopaque markers 170 and 172 may be formed as part of the deployment instrument, for example being placed on outer tube 71, and/or may be formed as part of the hemostatic implant 121. In either case, when the deployment apparatus is properly oriented as shown in FIG. 13A, the radiopaque markers 170 and 172 will appear to be stacked generally vertically when viewed in an anterior view, as shown in FIG. 13B. In contrast, if the apparatus has been improperly deployed so that the hemostatic implant has been advanced into the vessel lumen past the tissue tract TT as shown in FIG. 14A, then the radiopaque markers 170 and 172 will be spaced apart in the anterior view as shown in FIG. 14B. As these views will be readily distinguishable by the physician using conventional fluoroscopy, the radiopaque markers provide a convenient and reliable indicator of when it is acceptable to deploy the hemostatic implant.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for sealing a blood vessel penetration disposed at the end of a tissue tract, the method comprising:
- providing an apparatus including
  - a shaft,
  - a hemostatic implant disposed on an exterior surface of the shaft and having an outer surface,
  - a soluble plug for inhibiting hydration of the hemostatic implant and disposed on the exterior surface of the shaft, wherein the soluble plug has a perimeter surface, a distal surface and a proximal surface, wherein the proximal surface abuts a distal end of the hemostatic implant, and
  - a protective sleeve covering the outer surface of the hemostatic implant and the perimeter surface of the soluble plug, wherein the protective sleeve and the soluble plug protect the hemostatic implant from exposure to body fluids when present in the tissue tract;
- introducing the shaft through the tissue tract to position the hemostatic implant within the tissue tract, wherein the hemostatic implant and soluble plug are covered by the protective sleeve and the distal end of the hemostatic implant is covered by the soluble plug while the shaft is being introduced;
- retracting the protective sleeve to first expose the soluble plug followed by the hemostatic implant such that the soluble plug dissolves and is resorbed into surrounding tissue while the hemostatic implant expands and occludes the tissue track; and
- withdrawing the shaft past the expanded hemostatic implant which remains in the tissue tract.

2. The method as in claim 1, wherein the soluble plug is configured to seal against and prevent fluid ingress through an open end of the protective sleeve.

3. The method as in claim 1, wherein the soluble plug comprises a resorbable biopolymer.

4. The method as in claim 3, wherein the resorbable biopolymer comprises hyaluronic acid.

5. The method as in claim 1, wherein the apparatus further includes an occlusion element and the method further comprises deploying the occlusion element to inhibit blood flow from the blood vessel into the tissue tract.

6. The method as in claim 5, wherein at least a portion of the hemostatic implant is radiopaque, wherein the method further comprises observing the occlusion element to determine that it has a correct orientation before the protective sleeve is retracted.

7. The method as in claim 5, wherein deploying the occlusion element comprises shifting the occlusion element between a radially contracted configuration for passage through the tissue tract and a radially expanded configuration for deployment within the blood vessel to occlude the penetration.

8. The method as in claim 1, wherein the protective sleeve is latched to the shaft while the shaft is introduced, and the method further comprises unlatching the sleeve before retracting the sleeve, wherein unlatching comprises distally advancing a key over a latch on the shaft.

9. The method as in claim 1, wherein the hemostatic implant is prevented from being displaced proximally by a back stop on the shaft while the sleeve is retracted and while the shaft is withdrawn.

10. The method as in claim 1, wherein the protective sleeve comprises an outer sleeve and an inner release sheath, wherein the outer sleeve is retracted first while the inner release sheath inhibits sticking between the outer sleeve and the hemostatic implant.

11. The method as in claim 1, wherein the hemostatic implant comprises a cylindrical body which circumscribes the shaft.

12. The method as in claim 1, wherein the hemostatic implant comprises a body which is configured to open laterally and release from the shaft after the protective sleeve is withdrawn.

13. The method as in claim 1, wherein the hemostatic implant comprises a swellable, biodegradable polymer, wherein the polymer is not fully hydrated when covered by the protective sleeve and hydrates when exposed by retracting the protective sleeve.

14. The method as in claim 13, wherein the biodegradable polymer comprises a material selected from the group consisting of polyethylene glycols, collagens, and gelatins.

15. The method as in claim 14, wherein the hemostatic implant comprises an active agent comprising an anti-proliferative agent selected from the group consisting of sirolimus, paclitaxel, wherein the active agent is incorporated in a degradable carrier comprising a material selected from the group consisting of polylactic acid, and poly (lactide-co-glycolide).

16. The method as in claim 15, wherein the hemostatic implant comprises the active agent which comprises an anti-proliferative agent selected from the group consisting of sirolimus and paclitaxel, or an anticoagulant selected from the group consisting of thrombin and tissue factor.

17. An apparatus for sealing a blood vessel wall penetration disposed at an end of a tissue tract, said apparatus comprising:
- a shaft having a proximal end and a distal end;
- a hemostatic implant disposed over or adjacent to an exterior surface of the shaft, said hemostatic implant being hydratable to expand to occlude the tissue tract when exposed to body fluids within the tissue tract and having an outer surface;
- a protective sleeve retractably disposed over the hemostatic implant; and
- a soluble plug having a perimeter surface, a distal surface and a proximal surface, wherein the proximal surface abuts a distal end of the hemostatic implant and is positioned within the protective sleeve, such that the protective sleeve covers the outer surface of the hemostatic implant and the perimeter surface of the soluble plug, the soluble plug inhibiting hydration of the hemostatic implant prior to retraction of the protective sleeve, wherein the protective sleeve and the soluble plug protect the hemostatic implant from exposure to body fluids when present in the tissue tract.

18. The apparatus as in claim 17, further comprising an occlusion element near the distal end of the shaft, said occlusion element being shiftable between a radially contracted configuration for passage through the tissue tract and a radially expanded configuration for deployment within the blood vessel to occlude the penetration.

19. The apparatus as in claim 18, wherein the hemostatic implant comprises a body which circumscribes the shaft.

20. The apparatus as in claim 19, wherein the hemostatic implant comprises a body which is configured to open laterally from the shaft.

* * * * *